United States Patent [19]

Jones

[11] Patent Number: 5,514,087

[45] Date of Patent: May 7, 1996

[54] SELF-REGULATING INSUFFLATOR

[75] Inventor: Eric Jones, Southbridge, Mass.

[73] Assignee: Karl Storz GmbH & Co., Tuttlingen, Germany

[21] Appl. No.: 297,118

[22] Filed: Aug. 26, 1994

[51] Int. Cl.⁶ .......................... A61B 17/34; A61M 13/00
[52] U.S. Cl. .................. 604/26; 604/22; 128/747
[58] Field of Search ............ 128/204.18, 204.29, 128/205.24, 678, 207.14–207.17, 911, 912, DIG. 26, 747; 604/22–26; 137/116.5

[56] References Cited

U.S. PATENT DOCUMENTS

| 3,221,762 | 12/1965 | Chinn | 137/116.5 |
|---|---|---|---|
| 3,420,257 | 1/1969 | Lansky et al. | 137/116.5 |
| 3,621,867 | 11/1971 | Johnson | 137/116.5 |
| 3,885,590 | 5/1975 | Ford et al. | 137/613 |
| 3,906,982 | 9/1975 | Fleischhacker | 137/116.5 |
| 3,926,208 | 12/1975 | Hoffman et al. | 137/116.5 X |
| 3,982,533 | 9/1976 | Wiest | 604/26 |
| 4,171,004 | 10/1979 | Cerrato et al. | 137/116 |
| 4,178,940 | 12/1979 | Au | 128/207.15 |
| 4,869,717 | 9/1989 | Adair | 604/51 |
| 4,972,868 | 11/1990 | Davis et al. | 137/116.5 |
| 5,139,478 | 8/1992 | Konincky et al. | 604/26 |

FOREIGN PATENT DOCUMENTS

| 1163404 | 9/1958 | France | 137/116.5 |
|---|---|---|---|
| 1305095 | 8/1962 | France | 137/116.5 |
| 1382776 | 11/1964 | France | 137/116.5 |

Primary Examiner—Edgar S. Burr
Assistant Examiner—Eric P. Raciti
Attorney, Agent, or Firm—Donald D. Mon

[57] ABSTRACT

An insufflator for inflating body cavities, comprising a body to which a cannula and a needle are mounted, said needle being disposed in the cannula. The needle discharges gas from a regulator into the cavity gas from its distal end. A flow channel between the needle and cannula leads from the distal end of the cannula to the regulator. The regulator governs both the supply of gas to the cavity and the relief of excess pressure from the cavity.

5 Claims, 1 Drawing Sheet

SELF-REGULATING INSUFFLATOR

FIELD OF THE INVENTION

A self-regulated insufflator for endoscopic use.

BACKGROUND OF THE INVENTION

In the field of endoscopy it is necessary to introduce a gas into a body cavity in order that endoscopic procedures can be accomplished. Customarily an insufflator is provided for this purpose. It injects gas into the cavity through a cannula that penetrates into the cavity through an incision. Usually other incisions are also made to accommodate operating instruments and viewing instruments.

The injection of a gas into the human body must be very carefully regulated. Conventional insufflators include considerable circuitry to govern and limit the rate of flow of the gas, and the maximum pressure permitted in the cavity. The risks of over-pressure and of over-supply are well-known. Another more frequently encountered problem is that a too-little flow to accomplish the insufflation is supplied.

Known insufflators are quite bulky and are placed to one side on a support. The gas is fed to the cavity through a connecting tube to a cannula or trocar. It is fundamental that every surface which contacts insufflating gas must be non-contaminating. If a reverse pressure occurs and body fluids back up into the insufflator, considerable work must be done to clean up existing devices.

There are other problems. The usual insufflation pressure in the cavity is on the order of 15 mm Hg, and gas flow rates between about 10–20 liters per minute are needed. When gas at those pressures and rates must be passed through measuring orifices as well as through a cannula, it is not physically possible to supply such volumes at such low pressures through a suitably small-bore hose. Accordingly it is common practice to supply gas to the cavity itself at much higher pressures, on the order of 50 mm Hg, and to use a larger-bore hose in so doing. It is an inherent disadvantage of such systems. To avoid the risk of over-pressurizing, the gas is supplied in a series of short bursts, and the cavity pressure is measured so as to stop or reduce the number of bursts when an appropriate pressure is reached. The bore of the hose must therefore be quite large.

Such an arrangement also requires an elaborate control mechanism, which must control both the rate of flow and its output pressure to the trocar, because all of the response to cavity pressure is from within the control mechanism, which is located relatively far from the trocar.

It is an object of this invention to provide a self-regulating insufflator which receives gas under substantial pressure through a small-bore hose, which continuously regulates the pressure being supplied, and which is continuously responsive to cavity pressure.

It is another object of this invention to enable the use of a gas supply control mechanism to this insufflator which controls only the gas flow rate. Regulation of the actual supply and maintenance of cavity pressure is made a function of the insufflator itself. A control which merely supplies gas to establish and maintain a predetermined pressure, working from a high pressure source that supplies the gas at a given flow rate is much simpler than an insufflator which must also respond to varying conditions in the cavity. The fact that the supply hose is not also used to monitor cavity pressure results in considerable simplification.

The supply of gas to establish a predetermined pressure and to supplement the supply to make up for leakage is only one part of the problem. Over-pressure in the cavity is another. During endoscopic procedures, gases are supplied or generated from other sources, such as argon-beam coagulators, smoke evacuators, and coolant devices for lasers, all of which raise the cavity pressure. Relief of such over-pressure is also essential.

Significant economies can result, and safer supplies that can be entirely pneumatic can be made with this invention. Electronics will not be necessary, and explosive gases can be supplied without the precautions that are required when electrically controlled units are used. This instant invention is believed to be the first high rate of flow insufflator device which is entirely pneumatic, and which is therefore useful for supplying explosive gases.

It is another object of this invention to provide an insufflator which can conveniently be held by the hand, which is self-regulating, which can be supplied through a very small hose. It can be made so inexpensively that it can economically be discarded if the surgeon does not wish to have it cleaned and sterilized. Alternatively, parts of it may be made disposable, such as the regulator and hose, while a metal cannula or trocar could be sterilized and re-used for years.

This invention provides such an insufflator. It can be constructed also to accommodate a viewing or operating instrument, or a separate trocar, thereby reducing the number of incisions which must be made.

BRIEF DESCRIPTION OF THE INVENTION

An insufflator according to this invention includes a tubular cannula (which can also function as a trocar, if desired) for insertion into a body cavity. It surrounds a tubular needle for introducing gas into the cavity. The cannula and the needle are mounted to a regulator body.

The regulator body has a gas entry port which is customarily fitted with a filter to remove particulates from the gas. The entry port opens into an inlet chamber. The filter will preferably be hydrophobic which will pass gas, and will prevent any possibility of backflow of liquid to the gas supply system. A regulator port exits the inlet chamber and opens into a supply chamber to which the needle is connected. A regulator bias spring is seated in the inlet chamber.

A valve shuttle includes a first poppet which is biased by the regulator spring to tend to close the regulator port.

A valve shuttle further includes a rod attached to the first poppet and also to a second poppet. The second poppet also has a face. The rod passes sealingly through the wall of the supply chamber and enters a sensing chamber. The sensing chamber is fluidly connected to the passage in the cannula to convey cavity pressure to the sensing chamber. The sensing chamber is bounded by a wall of the regulator body and by one side of a diaphragm which extends across it.

A relief chamber is bounded by a wall of the regulator and by the other side of the diaphragm. Vent ports through the regulator wall vent the relief chamber to atmosphere.

A relief port is formed in the diaphragm, interconnecting the sensing chamber and the relief chamber. It includes a relief valve seat which is adapted to be closed by the face of the second poppet, depending on the relationship of the pressures and biases in the system. A bias spring biases the diaphragm and the relief valve seat toward the face of the second poppet.

As the consequence of the interaction of the shuttle valve and the diaphragm and two springs, the regulator valve will be open below some predetermined maximum intended cavity pressure. The regulator valve will be closed and the cavity pressure will be relieved should the cavity pressure for any reason exceed some predetermined limit above that maximum pressure, thereby providing a safety relief for over-pressure as well as a regulator valve shut off.

The invention will be fully understood from the following detailed description and the accompanying drawings, in which:

DETAILED DESCRIPTION OF THE INVENTION

Figure 1:
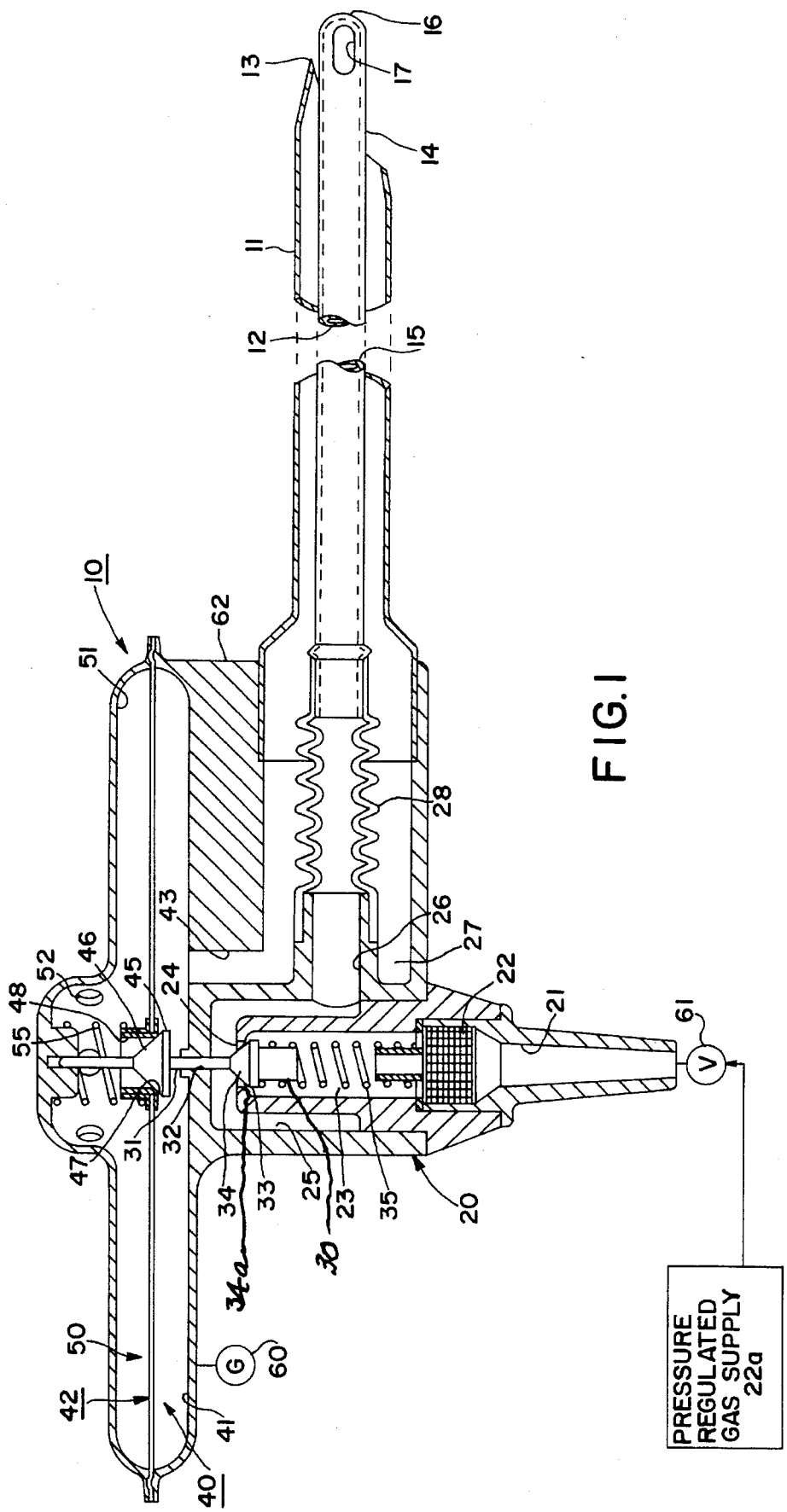
FIG. 1 is an axial cross-section of the presently preferred embodiment of the invention.

An insufflator 10 according to this invention is shown in the drawings. It includes a tubular cannula 11 having a lumen 12. If desired, the cannula can have a sharpened end with a piercing point 13, thereby also functioning as a trocar. Inside the lumen of the cannula is a tubular needle 14 having a lumen 15 and a rounded point 16. A side port 17 is provided through the wall of the needle for discharge of gas from the lumen into a body cavity that is to be inflated. The needle is mounted to a regulator body 20, as will later be described.

The regulator body has a gas entry port 21 that is customarily fitted with a filter 22 to remove particulates from an entering gas stream. Preferably the filter is hydrophobic, so as to prevent backflow of liquid into the gas supply system. The gas stream is usually carbon dioxide, supplied at an elevated pressure usually about 50 mm Hg, that is reduced by this regulator to a required cavity pressure, often about 15 mm Hg, and at a predetermined and regulated flow rate as determined by a pressure regulated gas supply 22a. Entry port 21 enters into an inlet chamber 23. Supply 22a is schematically shown.

Because the supply hose needs only to convey gas for supply, and need not also provide for sensing, a much smaller-bore hose can be used, especially in view of the high pressure it supplies to the regulator. Accordingly, a flexible hose with an outer diameter of only about 3.0 mm and an inner diameter of only about 2.5 mm can be used. Such a small size is light-weight and less obtrusive.

A regulator port 24 exits from the inlet chamber, and opens into a supply chamber 25. Supply chamber 25 exits through a supply port 26 in a tubular neck 27 to which a spring bellows 28 is attached. In turn, the needle is mounted to the bellows. The needle is thereby mounted to the regulator body and connected to the supply chamber through the bellows.

A valve shuttle 30 includes a rod 31 which is slidably and fluid-sealingly fitted in a passage 32 through the wall of the supply chamber. It further includes a first poppet 33 having a tapered face 34 facing into the regulator port. A regulator bias spring 35 seated in the inlet chamber biases the shuttle and thereby the first poppet to tend to close the regulator port at regulator valve seat 34a.

Closure of the regulator port will shut off gas flow to the needle. Opening of the regulator port by movement of the shuttle against bias spring 35 will pass the gas at a pressure and at a rate proportional to the distance by which the face of the first poppet is moved from the regulator port.

A sensing chamber 40 is formed in the body and is partly bounded by a body wall 41 through which passage 32 extends. It is additionally bounded by a flexible diaphragm 42 that is sealed to the body around its edge. The sensing chamber is fluidly connected to the lumen of the cannula by a passage 43, the cannula being mounted to the body at this location. By this means cavity pressure is conducted to the sensing chamber.

A second poppet 45 is fitted to rod 31 of valve shuttle 30. It has a tapered face 46 facing toward a seat 47 in a relief port 48. The relief port passes through the diaphragm, and when open interconnects sensing chamber 40 to a relief chamber 50. The relief chamber is partially bounded by a wall 51 in the body, and by the other side of diaphragm 42. Vent ports 52 pass through the wall of the body and interconnect the relief chamber and the atmosphere.

A bias spring 55 is interposed between the body and the diaphragm at the relief port in order to bias seat 47 toward face 46 of the second poppet.

It will be helpful to observe that the valve shuttle is unitary, and that both of its poppets move as one. Also, one seat- the regulator valve seat- is fixed, and the other one- the relief valve seat- is movable.

It will further be helpful to observe that the valve shuttle is oppositely opposed by two bias springs. One is spring 55 which bears against the diaphragm, and under most conditions through it against the second poppet. The other is spring 35, which oppositely biases first poppet 33.

In normal operations, relief port 48 will be closed, and the amount by which the regulator port is opened is a function of the opposed bias of the two springs, and the difference between cavity pressure and atmosphere, as responded to by the diaphragm. At all cavity pressures below the maximum allowed pressure, spring 55 will hold the relief valve seat against poppet face 46, and gas flow to the supply chamber will be permitted in response to cavity conditions. The regulator is shown in its equilibrium supply pressure when the cavity pressure is at its predetermined value.

The cavity pressure is affected by leakage from the cavity, both internally and around wounds through which instruments are inserted, and by absorption of the gas by the human body. This calls for a continuing but usually minor flow after the cavity is first inflated to the intended pressure. When additional gas is needed, the valve shuttle will be biased downwardly to open the regulator. The relief valve remains closed.

There is a cut-off shuttle valve position, set for some maximum desired supply pressure. Before this is reached, the relief valve remains closed and the regulator valve is also closed. When it is reached, the diaphragm will have moved with the second poppet, and the relief valve will still remain closed, because there is no need to vent the cavity.

If, however, for any reason the cavity pressure will have risen above the maximum permitted level, the regulator valve will remain closed, and abutment of the first valve poppet against the regulator valve seat will prevent the second poppet from following the diaphragm. Then the diaphragm will move the relief valve seat away from the second poppet, and the cavity pressure will be relieved until the pressure is again reduced to an allowable level. However, supply flow will not be resumed until the cavity pressure relative to ambient, together with the bias force of spring 55 move the first poppet in opposition to the bias force of spring 35 to reopen the regulator valve.

Excessive pressures can be generated by gases emanating from other sources, for example carbon dioxide gas used to cool lasers, argon-beam coagulators, and smoke evacuators. The relief valve relieves excessive pressure generated by such sources.

The single figure of drawings is an axial cross-section of a generally circular device, with the cannula at right angles to the "head" of the device. Instead, a different angle, perhaps 45 degrees could be selected. Also, the device can readily be modified to permit passage of operating instruments through the cannula by appropriately repositioning the gas control elements.

The illustrated cannula also functions as a trocar. However, its essential feature is to convey gases as a cannula. A separate trocar, or a removable trocar that can be assembled with the cannula, are available trocar arrangements.

A pressure gauge 60 can be plumbed into the sensing chamber. An off-on valve 61 should be plumbed into the supply line at the entry port. In order to avoid confusion of systems, all hoses should have couplers that are unique to this system. A stabilizing web 62 interconnects wall 41 and the wall of passage 43.

This invention is not to be limited to the embodiment shown in the drawings and described in the description, which is given by way of example and not of limitation, but only in accordance with the scope of the appended claims.

I claim:

1. A self-regulating insufflator for inflating a body cavity comprising:

a tubular cannula having a central lumen, a proximal end and a distal open end;

a gas supply needle having a central lumen, a proximal end and a distal end, and a discharge port adjacent to its distal end, said needle being disposed in the lumen of said cannula, at least one of the inside dimensions of the cannula's lumen being larger than the outside dimensions of the needle so as to leave a flow channel between them;

said distal ends being in near proximity to one another;

a regulator body having an inlet chamber, a gas entry port entering said inlet chamber, and a regulator port exiting said inlet chamber;

a regulator valve seat in said regulator port;

a regulator bias spring seated in said inlet chamber;

a valve shuttle comprising a rod, a first poppet including a first poppet face, and a second poppet including a second poppet face, said first poppet being disposed in said inlet chamber with said first poppet face facing said regulator valve seat, and said a regulator bias spring biasing said first poppet toward said regulator valve seat;

said body also forming an internal supply chamber, said regulator port interconnecting said inlet chamber and supply chamber, and said supply chamber being in fluid connection with the central lumen of the needle, the proximal end of said needle being mounted to said body;

said body additionally having a wall partially bounding a sensing chamber, said sensing chamber being additionally bounded by one side of a flexible diaphragm, said wall having a rod passage, the rod of the valve shuttle being slidably and fluid-sealingly fitted in said rod passage, said sensing chamber being in fluid connection with the central lumen of the cannula, the proximal end of said cannula being mounted to said body and the second poppet being disposed in said sensing chamber;

said body additionally having a wall partially bounding a relief chamber, said relief chamber being additionally bounded by the other side of said diaphragm;

a relief port through said diaphragm extending between the two sides of said diaphragm, a relief valve seat in said relief port, the poppet face of said second poppet facing said relief valve seat;

a second bias spring, said second bias spring being disposed between said body and said diaphragm to bias said diaphragm and thereby also the relief valve seat toward said poppet face of said second poppet; and vent means venting said relief chamber to atmosphere;

the spacing apart of the poppet faces being such that when the regulator valve is closed and pressure in the sensing chamber is at a predetermined pressure, the relief valve is also closed, and when the pressure in the sensing chamber is below that predetermined pressure the second bias spring will press the valve shuttle to open the regulator valve, the relief valve remaining closed, and when the pressure in the sensing chamber is sufficiently higher than said predetermined pressure, the diaphragm will deflect against the second bias spring to open the relief valve, the first bias spring will close the regulator port, and gas will vent from the sensing chamber into the relief chamber and out the vent ports.

2. An insufflator according to claim 1 in which a hydrophobic filter permeable to gas and impermeable to liquid is fitted to the body upstream from said inlet chamber.

3. An insufflator according to claim 1 in which an off-on valve is fitted to the body upstream from said inlet chamber.

4. An insufflator according to claim 1 in which said body has a gauge port extending into said sensing chamber, adapted to receive pressure-sensing means.

5. An insufflator according to claim 1 in which said distal end of said cannula is formed as a trocar.

* * * * *